United States Patent [19]
Sanger et al.

[11] Patent Number: 5,929,059
[45] Date of Patent: Jul. 27, 1999

[54] PHARMACEUTICAL COMPOSITIONS CONTAINING GRANISETRON AND DEXAMETHASONE

[75] Inventors: Gareth John Sanger, Sawbridgeworth; Christopher Stuart Dott, Redhill, both of United Kingdom

[73] Assignee: SmithKline Beecham p.l.c., Brentford, United Kingdom

[21] Appl. No.: 08/901,125

[22] Filed: Jul. 28, 1997

Related U.S. Application Data

[62] Continuation of application No. 08/361,602, Dec. 16, 1994, abandoned, which is a continuation-in-part of application No. 08/090,074, filed as application No. PCT/GB92/00091, Jan. 16, 1992.

[30] Foreign Application Priority Data

Jan. 19, 1991 [GB] United Kingdom ............. 9101221

[51] Int. Cl.⁶ ................. A61K 31/57; A61K 31/435; A61K 31/415
[52] U.S. Cl. ............................... 514/171; 514/299
[58] Field of Search .................. 514/171, 179, 514/180, 304, 299

[56] References Cited

FOREIGN PATENT DOCUMENTS

| 200 444 | 11/1986 | European Pat. Off. . |
| 2 627 986 | 8/1989 | France . |
| 2216414 | 10/1989 | United Kingdom . |

OTHER PUBLICATIONS

Van Liessum et al., *Scand. J. Gastroenterol. Suppl.*, 171, (1989) [Norway].
Dialog 03809716 Cancerlit ICDB/9107518; Cunningham, *Br. J. Cancer*, 62, 480 (1990, P. 480 [abstract].
Dialog 00789857 Cancerlit ICDB/90061960; Le Bonniec et al., *Proc. Annu. Meet. Am. Soc. Clin. Oncol.*, 9:A1277 (1990) [meeting abstract].
Carmichael et al., *Brit. Med. J.*, 297, 110 (1988).
Italian Group for Antiemetic Research, *N. Eng. J. Med.*, 332, 1 (1995).
Heron et al., *Annals of Oncology*, 5, 579 (1994).
Latreille et al., *Eur. J. Cancer*, 29A (Suppl 6), 1161 (1993).
Carmichael et al., *Eur. J. Cancer*, 29A (Suppl 6), 1149 (1993).
Smith et al., Br. J. Cancer, 61, pp. 323–324 (1990).
Ohmatsu et al., Jpn. J. Cancer Res., 85, pp. 1151–1158 (1994).
Yarker et al., Drugs, 48(5), pp. 761–793 (1994).
Aapro, Eur. J. Cancer, 27(3), pp. 356–361 (1991).
Cunningham et al., Lancet, vol. 1, p. 1323 (1989).
Abstract AN 951073249515, Eur. J. Clin. Res. (1994).
Plezia, et al., Clinics in Oncology 1985, 4(3),357, 371, 377, 380.
Costall, et al., Br. J. of Pharm., 1987, vol. 91, pp. 263–264.
Buchheit, et al., Br. J. of Pharm., 1985, vol. 37, pp. 664–667.
Bingham, et al., Mechanisms and Control of Emesis; 1992, vol. 223, pp. 249–250.
Miner, et al., Br. J. of Cancer; 1987, vol. 56, pp. 159–162.
Bermudez, et al., Br. J. of Cancer, 1988, vol. 58, pp. 644–650.
Smith, et al., Cancer Treatment Rep., 1986, vol. 70, pp. 934–935.

*Primary Examiner*—Phyllis G. Spivack
*Attorney, Agent, or Firm*—Wayne J. Dustman; William T. King; Charles M. Kinzig

[57] ABSTRACT

A method of treatment of nausea and vomiting is disclosed which comprises administering to a human or animal subject granisetron and an antiemetic corticosteroid.

19 Claims, No Drawings

PHARMACEUTICAL COMPOSITIONS CONTAINING GRANISETRON AND DEXAMETHASONE

This is a Continuation of application Ser. No. 08/361,602, filed Dec. 16, 1994, abandoned, which is a Continuation-in-part application of U.S. Ser. No. 08/090,074 filed Jul. 19, 1993, abandoned, which is a 371 of PCT/GB92/00091 filed Jan. 16, 1992.

This invention relates to a method of treatment and/or prophylaxis of nausea and vomiting, comprising the administration of a compound having 5-HT$_3$ receptor antagonist activity.

EP-A-200444 (Beecham Group p.l.c.), Example 6 discloses granisetron, and its use as an anti-emetic, especially useful in treating cytotoxic agent-induced nausea and vomiting. All references herein to granisetron include pharmaceutically acceptable salts, such as the hydrochloride, and solvates, such as hydrates.

The anti-emetic properties of granisetron are potentially enhanced by administering the compound in conjunction with systemic corticosteroids, such as dexamethasone. Dexamethasone is a systemic anti-inflammatory corticosteroid, which is known to have anti-emetic properties and to be useful in the treatment of emesis resulting from chemotherapy, especially cancer chemotherapy involving the use of, for example, cisplatin.

Accordingly, the present invention provides a pharmaceutical product comprising granisetron and steroid such as dexamethasone as a combined preparation for simultaneous, separate or sequential use in the treatment and/or prevention of nausea and vomiting.

The present invention also provides a method of treatment and/or prophylaxis of nausea and vomiting, which comprises administering to a human or animal subject, granisetron and steroid such as dexamethasone or a pharmaceutically acceptable salt or ester thereof.

The invention further provides the use of granisetron for the manufacture of a medicament for administration in conjunction with steroid such as dexamethasone or a pharmaceutically acceptable salt or ester thereof, for the treatment and/or prevention of nausea and vomiting.

Co-administration of granisetron with steroid such as dexamethasone is particularly useful for the treatment and/or prevention of nausea and vomiting associated with chemotherapy using cytotoxic drugs, especially cancer chemotheraphy involving the use of, for example, platinum complexes such as cisplatin or carboplatin, or cylcophosphamide or doxorubicin. Such co-administration may also reduce delayed or prolonged nausea and vomiting associated with this type of chemotherapy. Particular note should also be made of the use in the treatment of nausea and vomiting associated with other cytotoxic agents, such as that associated with radiation treatment.

Granisetron and steroid such as dexamethasone or a pharmaceutically acceptable salt or ester thereof, may be administered as a single pharmaceutical composition comprising effective amounts of the two active ingredients. Alternatively the two active ingredients may be co-administered in the form of two separate pharmaceutical compositions for simultaneous or sequential use.

Suitable pharmaceutically acceptable salts of granisetron for use according to the invention include acid addition salts formed with organic or inorganic acids for example, hydrochlorides, hydrobromides, sulphates, phosphates, citrates, fumarates and maleates. The solvates may, for example, be hydrates. A preferred form of granisetron for use according to the invention is the hydrochloride.

Dexamethasone may be administered according to the invention as dexamethasone alcohol or in the form of a pharmaceutically acceptable salt or ester. Suitable salts and esters include the acetate, isonicotinoate, phenylpropionate, pivalate, t-butyl acetate, trioxaundecanoate, disodium metasulphobenzoate and disodium phosphate.

A proposed dosage of granisetron for use according to the invention for administration to man (of approximately 70 kg body weight), is 0.05 to 25 mg., more preferably 0.05 to 20 mg, and most preferably 0.1 to 10 mg per unit dose, expressed as the weight of free base. A preferred dose of steroid such as dexamethasone for use according to the invention is in the range of 0.5 to 20 mg per dosage unit, expressed as the weight of the alcohol.

The unit doses may be administered, for example, 1 to 4 times per day. The exact dose will depend on the route of administration and the condition being treated, and it will be appreciated that it may be necessary to make routine variations to the dosage depending on the age and weight of the patient as well as the severity of the condition to be treated.

When the two active ingredients are administered as separate preparations, they are preferably given enterally, such as orally or parenterally (e.g. intramuscularly or, more particularly, intravenously).

According to a further aspect the invention provides a pharmaceutical composition, for use in human or veterinary medicine, comprising the granisetron, and steroid such as dexamethasone or a pharmaceutically acceptable salt or ester thereof.

Compositions according to the invention may be formulated in conventional manner using one or more physiologically acceptable carriers or excipients. Thus the compositions may, for example, be formulated for oral, buccal, parenteral or rectal administration. Compositions for administration by the oral route, in the form of for example tablets or capsules, are preferred.

Compositions for oral use such as tablets and capsules may be prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricant (e.g. magnesium stearate, talc or silica); disintegrants (e.g. potato starch or sodium starch glycollate); or wetting agent (e.g. sodium lauryl sulphate). Tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of one or both active ingredients.

For parenteral administration the compositions may be presented in a form suitable for bolus injection or continuous infusion. Formulations for injection may be presented in unit dosage form e.g. in syringes, ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredients may be in powder form for constitution with a suitable vehicle, e.g. sterile pyrogen-free water, before use.

For rectal administration the compositions may be formulated as suppositories or retention enemas, e.g. containing conventional suppository bases such as cocoa butter or other glycerides.

The pharmaceutical compositions of the invention may be prepared according to conventional techniques well known in the pharmaceutical industry. Thus, for example, the granisetron and the steroid such as dexamethasone or dexamethasone salt or ester may be admixed together, if desired, with suitable excipients. Tablets may be prepared, for example, by direct compression of such a mixture. Capsules may be prepared by filling the blend along with suitable excipients into gelatin capsules, using a suitable filling machine. Controlled release forms for oral or rectal administration may be formulated in a conventional manner associated with controlled release forms.

The compositions for use according to the invention may, if desired, be presented in a pack or dispenser device which may contain one or more unit dosage forms containing the active ingredients. The pack may for example comprise metal or plastic foil, such as a blister pack. The pack or dispenser device may be accompanied by instructions for administration. Where the granisetron and the steroid such as dexamethasone are intended for administration as two separate compositions these may be presented in the form of, for example, a twin pack.

CLINICAL STUDIES

First Study

A randomised, double blind, parallel group study comparing the use of granisetron and/or dexamethasone for prophylactic control of cisplatin (3 50 mg/m$^2$) induced nausea and vomiting is carried out for a period of seven days. Randomisation is stratified by cisplatin dose (50–74 mg/m$^2$ and 3 75 mg/m$^2$). Patients receive either granisetron for seven days, granisetron and dexamethasone for seven days, or granisetron and dexamethasone for one day followed by dexamethasone for six days.

The following are evaluated:

The improvement by dexamethasone of the efficacy of granisetron when both medications are given over a period of 24 hours and seven days.

The efficacy improvement of dexamethasone in preventing delayed onset nausea and/or vomiting when granisetron is administered from day 2–7.

Patients receiving cisplatin (350 mg/m$^2$) therapy for malignant disease are randomised in a double blind fashion, stratified according to cisplatin dosage, to receive the study medication.

The study design consists of 3 treatment arms:

1. Placebo (saline) 15 minutes infusion to be completed 20 minutes prior to cisplatin infusion (TIME 0) and granisetron 3 mg I.V. 15 minute infusion to be completed 5 min prior to TIME 0 followed by granisetron 1 mg p.o. at 6 and 12 h. Granisetron 1 mg p.o. B.I.D. begins at 24 h for 6 consecutive days.
2. Dexamethasone 10 mg I.V. 15 minute infusion to be completed 20 munutes prior to cisplatin infusion (TIME 0) and granisetron 3 mg I.V. 15 minute infusion to be completed 5 min prior to TIME) followed by granisetron 1 mg p.o. at 6 and 12 h.
3. Granisetron 1 mg p.o. B.I.D. and dexamethasone 8 mg p.o. B.I.D. begins at 24 h for 6 consecutive days.

Dexamethasone 10 mg I.V. 15 minute infusion to be completed 20 minutes prior to cisplatin infusion (TIME 0) and granisetron 3 mg I.V. 15 minute infusion to be completed 5 min prior to TIME 0 followed by granisetron 1 mg p.o. at 6 and 12. Dexamethasone 8 mg p.o. B.I.D. begins at 24 h for 6 consecutive days.

Patients disease state is assessed using the WHO classification and they must have a score of 2 or less. All patients are naive to cytotoxic therapy to avoid anticipatory emesis.

Patients who develop nausea and vomiting after their cisplatin therapy may be given up to four doses of prochlorperazine (10 mg suppositories) per day. If nausea and vomiting continue after this such that other anti-emetics have to be given, the physician decides whether or not to stop the study medication and/or treat with standard antiemetics. As far as is medically safe, patients remain on the study medication for as much of the 7 day treatment period as possible.

The primary efficacy assessments in the study are the percentage of Complete Responders, the time to first vomiting, and the use of other anti-emetics over the seven day period.

Secondary efficacy assessments of nausea and vomiting during the first 24 hours determine the increase in efficacy of granisetron by dexamethasone. As well, nausea and vomiting assessments after the first 24 hours determine the increase in efficacy of dexamethasone by granisetron in the maintenance phase of treatment.

The results of studies with i.v. granisetron are reported as follows:

1. Latreille et al Proc ASCO 1993; 12: 133 in which the conclusion was that dexamethasone markedly enhances the antiemetic efficacy of granisetron for acute onset emesis in high dose cisplatin therapy.
2. Carmichael et al Eur J Cancer 1993; 29A (Suppl 6): S206 in which the conclusion was that there is additive benefit with granisetron and dexamethasone in the prevention of cytostatic induced nausea and vomiting.

Second Study

A randomised, double blind, parallel group study is carried out, comparing oral granisetron (1.0 mg bid) with oral granisetron in combination with dexamethasone (12 mg iv) on the first day only and a conventional anti-emetic therapy, (metoclopramide 7 mg/kg iv plus dexamethasone 12 mg iv on the first day, followed by metoclopramide 10 mg tid po) over a 7 day period in controlling cisplatin induced nausea and vomiting.

The following are primary efficacy assessments:

The percentage of complete responders over the seven day period.

The time to less than complete response and use of other antiemetics using survival methods over the seven day period.

The following are secondary efficacy assessments:

The percentage of complete responders over the crtical 24 hour period.

Subjective symptom scoring for nausea and vomiting.

The results of this study are reported by Heron et al, Annals of Oncology 5: 579–584, 1994.

Third Study

A crossover clinical trial was carried out to compare the effectiveness and safety of granisetron alone (40 mug/kg) with that from a combination of granisetron plus methylprednisolone (MPL, 10 mg/kg) for control of emesis and vomiting induced by anticancer drugs in children with cancer. Complete control of emesis and vomiting were achieved in 95% (19/20 cases) of patients receiving the combination compared to 85% (17/20 cases) of patients receiving granisetron alone. There were no clinical toxicities or side effects in either treatment group. These data indicated that the combination of granisetron plus MPL was superior for control of emesis and vomiting in children receiving cytostatic anticancer drugs.

Fourth Study

This comparative study was undertaken to investigate the efficacy and safety of granisetron (40 mug/kg) and granisetron plus methylprednisolone (MPL; 10 mg/kg). Sixty-eight patients were given granisetron 170 times and thirty-nine patients were given a combination of granisetron and MPL 81 times. Sixty-one patients received the treatment in crossover fashion during the same chemotherapy regimens. The emetic and nausea episodes were counted during the 24 hours following each chemotherapy treatment. Complete response, no emesis or less than two episodes, were obtained in 75.3% (128/170 times) of patients receiving granisetron alone compared to 85.2% (69/81 times) of patients receiving the combination of granisetron plus MPL. There were no significant differences in complete responses between the two groups, male and female, and each age group. However, 11 of eighteen patients receiving granisetron alone who responded mildly, if at all, with respect to nausea and vomiting, showed a complete or major response when MPL was added to granisetron. There were two patients who developed temporal parasthesia of both hands as an adverse effect, but there was spontaneous recovery after 3 hours.

We claim:

1. A method of treatment or prophylaxis of cytotoxic agent-induced nausea and vomiting in a human or animal subject in need thereof, which comprises administering an effective amount of granisetron, or a pharmaceutically acceptable salt thereof, and a systemic corticosteroid.

2. A method according to claim 1 wherein the antiemetic corticosteroid is dexamethasone.

3. A method according to claim 1 wherein the antiemetic corticosteroid is methylprednisolone.

4. A method according to claim 1 wherein the cytotoxic agent is cisplatin.

5. A method according to claim 1 wherein the nausea and vomiting is delayed nausea and vomiting.

6. A method according to claim 1, wherein the granisetron is in the form of the hydrochloride salt.

7. A pharmaceutical formulation which comprises granisetron and an antiemetic corticosteroid.

8. A pharmaceutical composition according to claim 7 wherein the corticosteroid is dexamethasone.

9. A pharmaceutical composition according to claim 7 wherein the corticosteroid is methylprednisolone.

10. A kit for the treatment of nausea and vomiting which comprises, in separate containers, granisetron and an antiemetic corticosteroid.

11. A kit according to claim 10 wherein the corticosteroid is dexamethasone.

12. A kit according to claim 10 wherein the corticosteroid is methylprednisolone.

13. A method of treatment or prophylaxis of cytotoxic agent-induced delayed onset nausea and vomiting in a human or animal subject in need thereof, which comprises administering an effective amount of granisetron or a pharmaceutically acceptable salt thereof and a systemic corticosteroid for a period of more than 2 days after treatment with said cytotoxic agent.

14. A method as claimed in claim 13, wherein said corticosteroid is dexamethasone.

15. A method as claimed in claim 14, wherein the daily dose of dexamethasone is about 8 mg.

16. A method as claimed in claim 14 which comprises administering an initial dose of about 10 mg dexamethasone.

17. A method as claimed in claim 13, wherein the daily dose of granisetron or said pharmaceutically acceptable salt thereof is about 1 mg.

18. A method as claimed in claim 13 which comprises administering an initial dose of about 3 mg of granisetron followed by about 1 mg at about 6 hours and about 12 hours.

19. A method as claimed in claim 13 which comprises administering an effective amount of granisetron or a pharmaceutically acceptable salt thereof and a systemic corticosteroid for at least 7 days after treatment with said cytotoxic agent.

* * * * *